United States Patent
Wang

(10) Patent No.: US 10,785,920 B2
(45) Date of Patent: Sep. 29, 2020

(54) METHOD OF CULTIVATING PLANT IN TRANSPARENT SEALED CONTAINER AND BASE USED THEREFOR

(71) Applicant: SUNSHINE HORTICULTURE CO., LTD., Fujian (CN)

(72) Inventor: Dickson Wang, Fujian (CN)

(*) Notice: Subject to any disclaimer, the term of this patent is extended or adjusted under 35 U.S.C. 154(b) by 267 days.

(21) Appl. No.: 16/060,033

(22) PCT Filed: Oct. 14, 2016

(86) PCT No.: PCT/CN2016/102067
§ 371 (c)(1),
(2) Date: Jun. 7, 2018

(87) PCT Pub. No.: WO2018/068281
PCT Pub. Date: Apr. 19, 2018

(65) Prior Publication Data
US 2018/0352752 A1    Dec. 13, 2018

(51) Int. Cl.
| A01G 9/02 | (2018.01) |
| A01G 7/00 | (2006.01) |
| A01G 24/35 | (2018.01) |
| A01G 9/20 | (2006.01) |
| A01G 7/04 | (2006.01) |
| A01G 9/10 | (2006.01) |
| A01H 4/00 | (2006.01) |
| A01G 24/20 | (2018.01) |
| A01G 22/60 | (2018.01) |

(52) U.S. Cl.
CPC .............. *A01G 7/00* (2013.01); *A01G 7/045* (2013.01); *A01G 9/102* (2013.01); *A01G 9/20* (2013.01); *A01G 22/60* (2018.02); *A01G 24/20* (2018.02); *A01G 24/35* (2018.02); *A01H 4/001* (2013.01)

(58) Field of Classification Search
CPC ... A01G 7/00; A01G 7/06; A01G 9/02; A01G 9/021; A01G 9/20
USPC .................... 47/17, 29.1, 60, 63, 65.5, 66.7
See application file for complete search history.

(56) References Cited

U.S. PATENT DOCUMENTS

| 4,328,641 A * | 5/1982 | Tesch | A01G 31/00 47/59 R |
| 5,225,342 A * | 7/1993 | Farrell | A01G 5/06 435/430 |
| 5,375,372 A * | 12/1994 | Lee | A01H 4/001 47/69 |
| 5,561,946 A * | 10/1996 | Hsien | A01G 9/00 47/60 |
| 5,927,007 A * | 7/1999 | Oda | A01G 31/02 47/60 |
| 7,972,840 B2 * | 7/2011 | Hasegawa | C12M 25/02 435/297.1 |
| 8,544,208 B2 * | 10/2013 | Huang | A01G 9/02 47/60 |
| 9,629,314 B2 * | 4/2017 | Bijl | A01G 9/0299 |
| 2003/0221366 A1 * | 12/2003 | Weiner | A01G 9/00 47/65.7 |
| 2007/0292950 A1 * | 12/2007 | Bijl | A01G 9/02 435/420 |
| 2011/0010991 A1 * | 1/2011 | Fujii | A01G 9/0295 47/66.7 |
| 2012/0240462 A1 * | 9/2012 | Ogawa | A01G 7/02 47/58.1 SE |
| 2013/0174483 A1 * | 7/2013 | Caspar | A01H 4/006 47/65.8 |
| 2015/0040475 A1 * | 2/2015 | Schleeh | A01G 9/0291 47/66.7 |
| 2015/0313095 A1 * | 11/2015 | Fenner, Jr. | A01G 9/02 47/84 |
| 2017/0020092 A1 * | 1/2017 | Bijl | A01G 9/02 |
| 2017/0215351 A1 * | 8/2017 | Kremer | A01G 9/02 |
| 2018/0000028 A1 * | 1/2018 | Suntych | A01H 4/00 |

* cited by examiner

*Primary Examiner* — David J Parsley
*Assistant Examiner* — Danielle A Clerkley
(74) *Attorney, Agent, or Firm* — Prakash Nama; Global IP Services, PLLC

(57) ABSTRACT

A method of cultivating plant in transparent sealed container and base used therefor, wherein the base is mainly obtained by solidifying a mixture formed by adding gellan gum to transparent nutritional liquid; the gellan gum being added to the nutritional liquid is in an amount of 2-10 g/L; the base has a PH value of 3.5-10.0. The use of gellan gum as the sole transparent solidifying agent ensures the gellan gum, the base of the present invention is capable of adhering securely in the transparent sealed container. As shown by experiments, the base of the present invention will not slide or disperse in the transparent sealed container under normal shaking state, and can remain adhered to the transparent sealed container for 3-10 minutes when the transparent sealed container is turned upside down.

4 Claims, No Drawings

METHOD OF CULTIVATING PLANT IN TRANSPARENT SEALED CONTAINER AND BASE USED THEREFOR

BACKGROUND OF THE INVENTION

The present invention relates to a method of cultivating plant and base used therefor, and more particularly pertains to a method of cultivating plant in transparent sealed container and base used therefor.

Potted plants create an outdoor natural view in our small personal space, so that we could relax ourselves in the natural environment during our busy life.

With the advance of technology, there re plants which are cultivated n transparent sealed containers without the need of watering and nurturing. Such plants are increasingly popular. To enhance aesthetic appeal, the base for cultivating plants in transparent sealed containers is generally transparent base, such as transparent base obtained by solidifying transparent nutritional liquid and transparent gel such as carrageenan or agar. Such transparent base has poor adhesiveness and thus could not adhere securely in the transparent sealed container. During transportation, the plants inside the transparent sealed container are easily damaged due to motion or dispersion of the base. As it has a poor applicability, it is difficult to promote. To increase the adhesiveness of the transparent base, a plurality of gels are added to the transparent base, or other adhesive materials are added to the gel. However, the resulting transparent base has poorer transparency and uniformity, thus affecting aesthetic appeal.

BRIEF SUMMARY OF THE INVENTION

An object of the present inventions is to provide a method of cultivating plant in transparent sealed container. With the present invention, the transparent base has good adhesiveness with higher transparency and uniformity, and is capable of adhering securely in the transparent sealed container.

Another object of the present invention is to provide a base for cultivating plant in a transparent sealed container which has good adhesiveness with higher transparency and uniformity, and is capable of adhering securely in the transparent sealed container.

To attain the aforementioned objects, the present invention adopts the following technical scheme:

The base for cultivating plant in transparent sealed container is mainly obtained by solidifying a mixture formed by adding gellan gum to a transparent nutritional liquid; the gellan gum being added to the nutritional liquid is in an amount of 2-10 g/L; the base has a pH value of 3.5-10.0.

The nutritional liquid comprises a mixture formed by mixing and dissolving transparent water with no impurities, cultivating medium, and growth hormone and sugar source needed for plant growth, wherein all the aforesaid dissolves into a transparent solution.

The base has thickness of 1-10 mm in the transparent sealed container.

The method of cultivating plant in transparent sealed container comprises the following steps:

S1: selecting a transparent container: selecting a transparent container with an opening and the opening is engaged with a sealed plug;

S2: preparing a base:

S21: adding gellan gum to a transparent nutritional liquid to form the base for cultivating plant; the gellan gum being added to the nutritional liquid is in an amount of 2-10 g/L; the base is obtained in form of a transparent liquid; a pH value of the base is adjusted to 3.5-10.0;

S22: filling the base in liquid form as obtained in Step S21 into the transparent container so that the base in liquid form has a thickness of 1-10 mm in the transparent container, and sealing the opening of the transparent container with the sealed plug;

S23: sterilizing the transparent container obtained in Step S22 at a temperature of 122±2° C. and a pressure of 1.06±0.02 Kg/cm$^2$ for 15-40 minutes, then cooling down to room temperature until the base in liquid form in the transparent container solidifies;

S24: performing adhesive treatment the sterilized transparent container obtained in Step S23 at 20-25° C., RH30-50%, 5-20 umol/m$^2$/s; after 5-14 days the base and the transparent container adhere to each other and would not slide against each other; during the entire adhesive treatment the transparent container is positioned at normal vertical position;

S3: sterile plant cultivation: in a sterile environment, remove the sealed plug, and cultivate live sterile plantlet or sterile seed to the solidified base via the opening of the transparent container in sterile environment; during cultivation, cultivate according to plant growth direction to ensure harmonization among the plant, the base and the container; finally seal the sealed plug to ensure the entire cultivation process is conducted in a sterile environment;

S4: sterile plant culturing: position the transparent sealed container with cultivated live sterile plantlet or sterile seed under a temperature of 20-27° C., a humidity of RH30-70%, and a light intensity of 10-200 umol/m$^2$/s for 2-6 weeks; new leaves and new root system are grown, Angiospermae and the base match with each other, and the transparent base has an overall good growth and has a higher aesthetic value.

Gellan gum was initially developed by a US company Kelco in 1980s as a biogum hydrocolloid. It is an extracellular polysaccharide gum generated by the aerobic fermentation by pseudomonaseloden in the medium made of glucose as carbon source, ammonium nitrate as nitrogen source and some inorganic salt under neutral conditions. Gellan gum is usually used as food additive for improving taste; it has also been used in plant cultivation, but when used in plant cultivation it serves as nutrients needed by plants.

The method of cultivating plant in transparent sealed container and base used therefor of the present invention use gellan gum as the sole transparent solidifying agent, thereby ensuring the uniformity and transparency of the transparent base; besides, with the good adhesiveness of gellan gum, the base of the present invention is capable of adhering securely in the transparent sealed container. As shown by experiments, the base of the present invention will not slide or disperse in the transparent sealed container under normal shaking state, and can remain adhered to the transparent sealed container for 3-10 minutes when the transparent sealed container is turned upside down.

DETAILED DESCRIPTION OF THE INVENTION

The base for cultivating plant in transparent sealed container is mainly obtained by solidifying a mixture formed by adding gellan gum to a transparent nutritional liquid; the gellan gum being added to the nutritional liquid is in an amount of 2-10 g/L; the base has a pH value of 3.5-10.0.

The nutritional liquid comprises a mixture formed by mixing and dissolving transparent water with no impurities, cultivating medium, and growth hormone and sugar source needed for plant growth, and optionally nutrients for plants such as nitrogen phosphorus, potassium and so forth or fertilizers, wherein all the aforesaid dissolves into a transparent solution.

In the base, if EC value (soluble salt content) is lower than 0.5 ms/cm, the gellan gum being added is in an amount of 8.0-10.0 g/L; if EC value is higher than 3.0 ms/cm, the gellan gum being added is in an amount of 2.0-5.0 g/L, preferably 3.0-4.0 g/L.

Depending on plant type, the base thickness of 1-10 mm in the transparent sealed container.

The method of cultivating plant in transparent sealed container comprises the following steps:

S1: Selecting a Transparent Container:

Selecting a transparent container which is made of glass or plastic and sealable. The transparent container does not deform under high temperature sterilization or physical or chemical sterilization and maintains a fixed shape. Besides, the transparent container has an opening and the opening is engaged with a sealed plug.

The opening may be opened at a position higher than ¼ from the base of the transparent container; alternatively the opening may be opened at the top of the transparent container. The opening has a diameter of 10-50 mm. The sealed plug may be made of wood, cotton, plastic and so forth.

S2: Preparing a Base:

S21: Using transparent water with no impurities (such as deionized water, sterile water, pure water or transparent tap water, deep well water, river water) as solvent and adding the same to ⅔ of a specific volume, then adding in, mixing and dissolving cultivating medium and growth hormone and sugar source needed for plant growth. Nutrients for plants such as nitrogen, phosphorus, potassium and so forth or fertilizers may also be added. All the aforesaid dissolves into a transparent solution, and a transparent nutritional liquid is obtained.

S22: Adding gellan gum to the transparent nutritional liquid obtained in Step S1 to form the base for cultivating plant. The gellan gum being added to the nutritional liquid is in an amount of 2-10 g/L. The base is obtained in form of a liquid. The pH value of the base adjusted to 3.5-10.0 by 1N HCl or 1N NaOH, and then bring to volume.

In the base in form of a liquid, if EC value (soluble salt content) is lower than 0.5 ms/cm, the gellan gum being added is in an amount of 8.0-10.0 g/L, if EC value is higher than 3.0 ms/cm, the gellan gum being added is in an amount of 2.0-5.0 g/L, preferably 3.0-4.0 g/L.

S22: Filling the base in liquid form as obtained in Step S21 into the transparent container so that the base in liquid form has a thickness of 1-10 mm in the transparent container, and sealing the opening of the transparent container with the sealed plug. Position the transparent container with the opening facing upward to prevent the nutritional liquid from flowing out.

S23: Sterilizing the transparent container obtained in Step S22 at a temperature of 122±2° C. and a pressure of 1.06±0.02 Kg/cm$^4$ for 15-40 minutes, then cooling down to room temperature until the base in liquid form in the transparent container solidifies.

S24: Performing adhesive treatment on the sterilized transparent container obtained in Step S23 at 20-25° C., RH30-50%, 5-20 umol/m$^2$/s; after 5-14 days the base and the transparent container adhere to each other and would not slide against each other; during the entire adhesive treatment the transparent container is positioned at normal vertical position.

S3: Sterile Plant Cultivation:

In a sterile environment, remove the sealed plug, and cultivate live sterile plantlet or sterile seed to the solidified base via the opening of the transparent container in a sterile environment; during cultivation, cultivate according to plant growth direction to ensure harmonization among the plant, the base and the container; finally seal the sealed plug to ensure the entire cultivation process is conducted in a sterile environment.

S4: Sterile Plant Culturing:

Positioning the transparent sealed container with cultivated live sterile plantlet or sterile seed under a temperature of 20-27° C., a humidity of RH30-70%, and a light intensity of 10-200 umol/m$^2$/s for 2-6 weeks; new leaves and new root system are grown, Angiospermae and the base match with each other, and the transparent base has an overall good growth and has a higher aesthetic value.

The method of cultivating plant in transparent sealed container and base used therefor of the present invention use gellan gum as the sole transparent solidifying agent, thereby ensuring the uniformity and transparency of the transparent base; besides, with the good adhesiveness of gellan gum, the base of the present invention is capable of adhering securely in the transparent sealed container. As shown by experiments, the base of the present invention will not slide or disperse in the transparent sealed container under normal shaking state, and can remain adhered to the transparent sealed container for 3-10 minutes when the transparent sealed container is turned upside down.

When the present invention is used for cultivation, the uniform transparent base and the transparent container are in harmony. The transparent sealed container cultivated with plant therein may be placed under room temperature for viewing for 6-24 months. It is also possible to observe the entire growing process of plant growth. It is therefore a desired ornament in home or office.

What is claimed is:

1. A method of cultivating a plant in a transparent sealed container, characterized in that it comprises the following steps:

S1: selecting a transparent container with an opening, wherein the opening is engaged with a sealed plug;

S2: preparing a base:

S21: adding gellan gum to a transparent nutritional liquid to form the base for cultivating the plant; wherein the gellan gum being added to the transparent nutritional liquid is in an amount of 2-10 g/L; and adjusting a pH value of the base to 3.5-10.0;

S22: filling the base in liquid form as obtained in Step S21 into the transparent container, and sealing the opening of the transparent container with the sealed plug;

S23: sterilizing the transparent container obtained in Step S22 at a temperature of 122±2° C. and a pressure of 1.06±0.02 Kg/cm$^2$ for 15-40 minutes, then cooling the transparent container down to room temperature until the base in liquid form in the transparent container solidifies;

S24: performing adhesive treatment on the sterilized transparent container obtained in Step S23 at a temperature of 20-25° C., a relative humidity of 30-50%, and a light intensity of 5-20 umol/m$^2$/s for 5-14 days, resulting in the base and the transparent container adhered to each other without sliding against each other; during the entire Step S24, the transparent container is positioned at a vertical position; S3: removing the sealed plug, and cultivating one of a live sterile plantlet and a sterile seed to the solidified base via the opening of the transparent container in a sterile environment; wherein one of the live sterile plantlet and the sterile seed is cultivated according to a plant growth direction to ensure harmonization among the plant, the base and the transparent container; finally sealing the sealed plug to ensure that one of the live sterile plantlet and the sterile seed is cultivated in the sterile environment; S4: placing the transparent sealed container with one of the cultivated live sterile plantlet and the sterile seed under temperature of 20-27° C., a relative humidity of 30-70%, and a light intensity of 10-200 umol/$m^2$/s for 2-6 weeks to grow new leaves and a new root system, wherein Angiospermae and the base match with each other.

2. The method as in claim 1, characterized in that: the transparent nutritional liquid comprises a transparent solution formed by mixing and dissolving water with no impurities, a cultivating medium, a growth hormone, and a sugar source needed for plant growth.

3. The method as in claim 1, characterized in that: the base has a thickness of 1-10 mm in the transparent sealed container.

4. The method as in claim 2, characterized in that the base has a thickness of 1-10 mm in the transparent sealed container.

\* \* \* \* \*